(12) United States Patent
Duddu et al.

(10) Patent No.: US 6,262,102 B1
(45) Date of Patent: Jul. 17, 2001

(54) EPROSARTAN MONOHYDRATE

(75) Inventors: Sarma Duddu, Foster City, CA (US); Nageswara R Palepu, Northwood (GB); Gopadi M Venkatesh, King of Prussia, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/445,637

(22) PCT Filed: Jun. 26, 1998

(86) PCT No.: PCT/US98/13459
§ 371 Date: Dec. 8, 1999
§ 102(e) Date: Dec. 8, 1999

(87) PCT Pub. No.: WO99/00383
PCT Pub. Date: Jan. 7, 1999

Related U.S. Application Data

(60) Provisional application No. 60/051,170, filed on Jun. 27, 1997.

(51) Int. Cl.[7] ............................ C07D 407/06; A61P 9/12; A61P 13/12; A61K 31/4178

(52) U.S. Cl. .......................................... 514/397; 548/315.1
(58) Field of Search ........................... 514/397; 548/315.1

(56) References Cited

U.S. PATENT DOCUMENTS 5,185,351  2/1993  Finkelstein et al. ................. 514/341

OTHER PUBLICATIONS

Sheng, Jie et al, J. Pharm. Sci., 88, 1999, 1021–1029.*

* cited by examiner

Primary Examiner—Mukund J. Shah
Assistant Examiner—Thomas McKenzie
(74) Attorney, Agent, or Firm—Mary E. McCarthy; Stephen Venetianer; Charles M. Kinzig

(57) ABSTRACT

This invention relates to (E)-α-[2-n-butyl-1-[(4-carboxyphenyl)methyl]-1) H-imidazol-5-yl]methylene-2-thiophenepropionic acid monomethanfesulfonate monohydrate, compositions containing the compound and methods of using the compound to block angiotensin II receptors and to treat hypertension, congestive heart failure and renal failure.

5 Claims, No Drawings

EPROSARTAN MONOHYDRATE

This is a 371 of International Application PCT/US9813459, filed Jun. 26, 1998, which claims benefit from the Provisional Application U.S. Ser. No. 60/051,170 filed Jun. 27, 1997.

FIELD OF THE INVENTION

This invention relates to a pharmaceutically active compound, compositions containing the compound and methods of using the compound in the treatment of certain disease states in mammals, in particular man. More specifically, the present invention relates to (E)-α-[2-n-butyl-1-[(4-carboxyphenyl)methyl]-1H-imidazol-5-yl] methylene-2-thiophenepropionic acid monomethanesulfonate monohydrate, compositions containing this compound, and methods of using (E)-α-[2-n-butyl-1-[(4-carboxyphenyl)methyl]-1H-imidazol-5-yl]methylene-2-thiophenepropionic acid monomethanesulfonate monohydrate to block angiotensin II (AII) receptors and to treat hypertension, congestive heart failure and renal failure.

BACKGROUND OF THE INVENTION

The compound (E)-α-[2-n-butyl-1-[(4-carboxyphenyl) methyl]-1H-imidazol-5-yl]methylene-2-thiophenepropionic acid monomethanesulfonate is known by the name "eprosartan" and is the subject of U.S. Pat. No. 5,185,351 (the '351 patent), issued Feb. 9, 1993. This patent discloses in Example 41 a process for making the anhydrous form of (E)-α-[2-n-butyl-1-[(4-carboxyphenyl)methyl]-1H-imidazol-5-yl]methylene-2-thiophenepropionic acid monomethanesulfonate. Additionally, the '351 patent discloses conventional techniques for formulating (E)-α-[2-n-butyl-1-[(4-carboxyphenyl)methyl]-1H-imidazol-5-yl] methylene-2-thiophenepropionic acid monomethanesulfonate and Example; 108–111 specifically detail the preparation of certain formulations. This compound is claimed to have utility in blocking angiotensin II receptors and to be useful in the treatment of hypertension, congestive heart failure and renal failure.

It has been found that the monohydrate of (E)-α-[2-n-butyl-1-[(4-carboxyphenyl)methyl]-1H-imidazol-5-yl] methylene-2-thiophenepropionic acid monomethanesulfonate is formed during the vacuum drying of the dihydrated form of this compound or when the anhydrate of (E)-α-[2-n-butyl-1-[(4-carboxy-phenyl)methyl]-1H-imidazol-5-yl]methylene-2-thiophenepropionic acid monomethanesulfonate is granulated with water, stored at 50° C. overnight and vacuum dried overnight at ambient temperature.

SUMMARY OF THE INVENTION

The present invention provides a novel monohydrate of (E)-α-[2-n-butyl-1-[(4-carboxyphenyl)methyl]-1H-imidazol-5-yl]methylene-2-thiophenepropionic acid monomethanesulfonate, in particular, in pharmaceutical compositions for the treatment of diseases in which blockade of angiotensin II receptors is indicated, for example, in the treatment of hypertension, congestive heart failure and renal failure.

DETAILED DESCRIPTION OF THE INVENTION (E)-α-[2-n-Butyl-1-[(4-carboxyphenyl)methyl]-1H-imidazol-5-yl]methylene-2-thiophenepropionic acid monomethanesulfonate is known to exist in an anhydrous form and is characterized by the data shown in FIGS. 1, 4 and 7. This compound has the following structure:

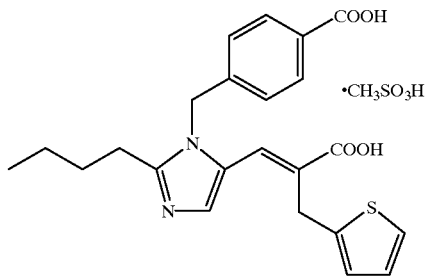

(E)-α-[2-n-Butyl-1-[(4-carboxyphenyl)methyl]-1H-imidazol-5-yl]methylene-2-thiophenepropionic acid monomethanesulfonate, eprosartan, is claimed in U.S. Pat. No. 5,185,351. Reference should be made to said patent for its full disclosure, including the methods of preparing and using this compound. The entire disclosure of the '351 patent is incorporated herein by reference.

Eprosartan is anhydrous, and, by itself, is stable at ambient temperature and humidity, as well as at accelerated conditions (30° C./79%RH or 40° C./75%RH for up to 6 months). This drug substance does not pick up moisture at higher humidities (typically up to 95%RH). However, the anhydrous form of the compound converts to the hydrated form, if it is moistened prior to storage in a closed container at ambient or higher temperatures, or if the dry powder is stored at a relative humidity of 98% or higher at ambient or higher temperatures for 8 days or longer. In the former case where the hydrate is obtained by moistening the drug substance, the hydrated form is not stable, and is generally converted back into the anhydrous form during drying.

In accordance with the present invention, it has been found that a monohydrated form of (E)-α-[2-n-butyl-1-[(4-carboxyphenyl)methyl]-1H-imidazol-5-yl]methylene-2-thiophenepropionic acid monomethanesulfonate is produced during the vacuum drying of the dihydrated form of this compound or when the anhydrate of (E)-α-[2-n-butyl-1-[(4-carboxy-phenyl)methyl]-1H-imidazol-5-yl]methylene-2-thiophenepropionic acid monomethanesulfonate is granulated with water, stored at 50° C. overnight and vacuum dried overnight at ambient temperature.

According to the instant invention, the dihydrate prepared using different excipients behave differently in terms of ease of conversion of the dihydrate to the monohydrate during vacuum drying. Continued vacuum drying of moist granulations results in partial to complete conversion of the dihydrate initially formed to the monohydrate. For example, the dihydrate formed in granulations containing excipients, such as soluble starch, xanthan gum and gelatin, stored for for up to 24 hrs, was found to convert to the monohydrate form upon vacuum drying. Eprosartan granulated with water, stored at 50° C. overnight and vacuum dried overnight at ambient temperature was also found to be a monohydrate. However, there is always a possibility of getting a mixture of a monohydrate, a dihydrate and an an hydrate depending on the length or severity of vacuum drying.

The two tables, below, summarize the powder X-ray diffraction (XRD) pattern and the FTIR [Fourier transform infrared] spectroscopic data of the anhydrate, the monohydrate and the dihydrate of (E)-α-[2-n-Butyl-1-[(4- carboxyphenyl)methyl]-1H-imidazol-5-yl]methylene-2-thiophenepropionic acid monomethanesulfonate.

TABLE 1

Powder X-Ray Data
X-Ray Peak Position, 2θ
(Relative Intensity)

| Anhydrate | Monoclinic | Dihydrate |
|---|---|---|
| 7.15 (82) | 8.55 (37) | 8.45 (36) |
|  | 9.40 (20) | 9.95 (20) |
|  |  | 10.80 (22) |
| 13.90 (22) | 12.60 (13) | 12.35 (14) |
| 14.35 (24) | 14.35 (16) | 14.00 (15) |
|  | 15.80 (35) | 15.90 (27) |
|  | 17.25 (100) | 16.80 (93) |
| 18.30 (50) | 18.25 (58) | 18.10 (27) |
| 18.9 (100) | 19.25 (43) | 18.45 (36) |
| 20.10 (58) | 19.70 (92) | 18.70 (40) |
| 20.45 (41) | 20.90 (34) | 20.05 (59) |
| 21.00 (44) | 21.55 (41) | 20.75 (68) |
|  | 21.75 (68) | 21.45 (81) |
| 22.20 (55) | 22.15 (60) | 21.90 (100) |
|  | 22.60 (71) | 22.60 (71) |
|  | 22.90 (79) |  |
|  | 23.45 (84) | 24.65 (71) |
| 24.35 (43) | 26.60 (34) | 26.60 (35) |
|  | 27.25 (38) | 27.45 (16) |
|  | 28.70 (35) | 29.10 (21) |
| 28.95 (21) |  |  |
|  | 31.05 (37) | 30.40 (29) |
| 34.20 (8) | 35.05 (20) | 35.85 (10) |

(Note: Characteristic diffraction peaks are highlighted)

TABLE 2

FTIR Data

| Anhydrate | Monohydrate | Dihydrate |
|---|---|---|
| 1714 | 1725 | 1705 |
| 1692 | 1703 | 1690 |
| 1650 | 1638 | 1640 |
|  | 1613 | 1614 |
| 1539 | 1534 | 1538 |
| 1505 | 1504 | 1511 |
| 1429 | 1419 | 1438 |
| 1384 | 1379 | 1384 |
|  |  | 1289 |
| 1215 | 1229 | 1238 |
| 1050 | 1044 | 1042 |
| 851 | 845 | 846 |
| 712 | 711 | 704 |

(E)-α-[2-n-Butyl-1-[(4-carboxyphenyl)methyl]-1H-imidazol-5-yl]methylene-2thiophenepropionic acid monomethanesulfonate monohydrate may be co-administered with other pharmaceutically active compounds, for example, in physical combination or by sequential administration. Conveniently, the compound of this ivention and the other active compound are formulated in a pharmaceutical composition. Thus, this invention also relates to pharmaceutical compositions comprising (E)-α-[2-n-butyl-1-[(4-carboxyphenyl)methyl]-1H-imidazol-5-yl] methylene-2-thiophenepropionic acid monomethanesulfonate monohydrate, a pharmaceutically acceptable carrier, and a second pharmaceutically active compound selected from the group consisting of a diuretic, a calcium channel blocker, a β-adrenoceptor blocker, a resin inhibitor, and an angiotensin converting enzyme inhibitor. Examples of compounds which may be included in pharmaceutical compositions in combination with (E)-α-[2-n-butyl-1-[(4-carboxyphenyl)methyl]-1H-imidazol-5-yl]methylene-2-thiophenepropionic acid monomethanesulfonate monohydrate are diuretics, particularly a thiazide diuretic, such as hydrochlorothiazide, or a loop diuretic, such as furosemide, calcium channel blockers, particularly dihydropyridine antagonists, such as nifedipine, β-adrenoceptor blockers, such as propranolol, resin inhibitors, such as enalkinen, and angiotensin converting enzyme inhibitors, such as captopril or enalapril. Preferably, the pharmaceutical composition contains 200–400 mg of (E)-α-[2-n-butyl-1-[(4-carboxyphenyl)-methyl]-1H-imidazol-5-yl]methylene-2-thiophene-propionic acid monomethanesulfonate monohydrate in combination with 6.25–25 mg of hydrochlorothiazide.

No unacceptable toxicological effects are expected when (E)-α-[2-n-butyl-1-[(4-carboxyphenyl)methyl]-1H-imidazol-5-yl]methylene-2-thiophenepropionic acid monomethanesulfonate monohydrate is administered in accordance with the present invention.

(E)-α-[2-n-Butyl-1-[(4-carboxyphenyl)methyl]-1H-imidazol-5-yl]methylene-2-thiophenepropionic acid monomethanesulfonate monohydrate is useful for treating diseases in which blockade of the angiotensin II receptor would be beneficial. Preferably, this compound is used alone or in combination with said second pharmaceutically active compounds in the treatment of hypertension, congestive heart failure and renal failure. Additionally, (E)-α-[2-n-butyl-1-[(4-carboxy-phenyl)methyl]-1H-imidazol-5-yl] methylene-2-thiophenepropionic acid monomethane-sulfonate monohydrate is of value in the treatment of left ventricular hypertrophy regression, diabetic nephropathy, diabetic retinopathy, mascular degeneration, haemorrhagic stroke, primary and secondary prevention of infarction, prevention of atheroma progression and the regression of atheroma, prevention of restinosis after angioplasty or bypass surgery, improving cognitive function, angina, glaucoma, and CNS disorders, such as anxiety.

The following examples are illustrative of the instant invention. These examples are not intended to limit the scope of this invention as defined hereinabove and as claimed hereinbelow.

In Examples 1–3, below, the term "internals" means the ingredients which are granulated with the anhydrous form of (E)-(-[2-n-butyl-1-[(4-carboxyphenyl)-methyl]-1H-imidazol-5-yl]methylene-2-thiophenepropionic acid monomethanesulfonate.

EXAMPLES

Examples 1–3
Preparation of (E)-α-[2-n-Butyl-1-[(4-carboxyphenyl)methyl]-1H-imidazol-5-yl]methylene-2-thiophenepropionic Acid Monomethanesulfonate Monohydrate

TABLE I

| Internals | Example 1 (%) | Example 2 (%) | Example 3 (%) |
|---|---|---|---|
| Compound A* | 30–50 | 60–80 | 50–70 |
| Lactose, hydrous | 15–30 | 7–20 | 1–5 |
| Cellulose (Avicel) | 2–15 | 7–20 | — |
| Starch 1551 | 2–7 | — | — |
| Povidone (PVP) | — | 2–8 | — |
| Purified water | ** | ** | ** |

* (E)-α-[2-n-butyl-1-[(4-carboxyphenyl)methyl]-1H-imidazol-5-yl] methylene-2-thiophenepropionic acid monomethanesulfonate, anhydrous form TABLE I-continued

| Internals | Example 1 (%) | Example 2 (%) | Example 3 (%) |
|---|---|---|---|

** Composition does not take into account the formation of the dihydrate during granulation.

Table I, above, summarizes the amounts of Compound A and excipients on a weight for weight basis used in Examples 1–3 below.

Example 1

A fluid bed granulator, UniGlatt, is charged with the anhydrous form of (E)-α-[2-n-butyl-1-[(4-carboxyphenyl)methyl]-1H-imidazol-5-yl]methylene-2-thiophenepropionic acid monomethanesulfonate and Impalpable Lactose, homogenized with an aqueous suspension of Starch 1551 and granulated by spraying at a desirable flow rate and dry wet mass to an LOD (loss on drying) of 5.5–6.5% determined using a Sartorius moisture meter tested at 110° C. The monohydrate is formed during the vacuum drying of the dihydrated form of this compound.

Example 2

The internals are premixed in the Collette bowl for 1 min at a low chopper setting and granulated for 4 min by adding water (added in parts) at a high chopper setting. The granulate is then milled through an appropriate screen and dried to an LOD of 5.5–6.5%. The monohydrate is formed during the vacuum drying of the dihydrated form of this compound.

Example 3

The internals are premixed in a high shear granulator and granulated at a high chopper setting with hydrous lactose added in solution. The monohydrate is formed during the vacuum drying of the dihydrated form of this compound.

Example 4

Preparation of (E)-α-[2-n-Butyl-1-[(4-carboxyphenyl)methyl]-1H-imidazol-5-yl]methylene-2-thiophenepropionic Acid Monomethanesulfonate Dihydrate Eprosartan an hydrate was suspended in an aqueous solution of 3.0 M methanesulfonic acid. The suspension was continuously stirred and heated to 65–70° C. The filtrate obtained by suction was maintained at 75° C. for several minutes to ensure the absence of the anhydrate in solution. The solution was slowly cooled to ambient temperature and clear colorless crystalline drug substance was harvested by filtration and air dried. The monohydrate is formed during the vacuum drying of the dihydrated form of this compound.

It is to be understood that the invention is not limited to the embodiments illustrated hereinabove and the right is reserved to the illustrated embodiments and all modifications coming within the scope of the following claims.

What is claimed is:

1. A compound which is (E)-α-[2-n-butyl-1-[(4-carboxyphenyl)methyl]-1H-imidazol-5-yl]methylene-2-thiophenepropionic acid monomethanesulfonate monohydrate.

2. A method of blocking angiotensin II receptors which comprises administering to a subject in need thereof an effective amount of the compound according to claim 1.

3. A method of treating hypertension which comprises administering to a subject in need thereof an effective amount of the compound according to claim 1.

4. A method of treating congestive heart failure which comprises administering to a subject in need thereof an effective amount of the compound according to claim 1.

5. A method of treating renal failure which comprises administering to a subject in need thereof an effective amount of the compound according to claim 1.

* * * * *